United States Patent
Wittmann et al.

(10) Patent No.: US 7,806,853 B2
(45) Date of Patent: *Oct. 5, 2010

(54) ARRAY AND METHOD FOR DOSING A HORMONE REGULATING BLOOD SUGAR IN A PATIENT

(75) Inventors: Uwe Wittmann, Lamperteim (DE); Helmut Rinne, Mannheim (DE); Ralf Gessler, Baienfurt (DE); Hans-Joerg Pfleiderer, Ulm (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/471,150

(22) Filed: May 22, 2009

(65) Prior Publication Data
US 2009/0254024 A1    Oct. 8, 2009

Related U.S. Application Data

(63) Continuation of application No. 10/203,673, filed as application No. PCT/EP01/00625 on Jan. 20, 2001, now Pat. No. 7,556,613.

(30) Foreign Application Priority Data
Feb. 10, 2000    (DE)    ................ 100 06 044

(51) Int. Cl.
*A61M 31/00*    (2006.01)
(52) U.S. Cl. .................... 604/65; 604/66; 604/890.1
(58) Field of Classification Search ............ 604/29, 604/30, 65, 66, 67, 131, 151, 890.1
See application file for complete search history.

(56) References Cited

U.S. PATENT DOCUMENTS

| 4,077,405 A | * | 3/1978 | Haerten et al. ............ 604/66 |
| 4,280,494 A | | 7/1981 | Cosgrove, Jr. et al. |
| 4,282,872 A | | 8/1981 | Franetzki et al. |

(Continued)

FOREIGN PATENT DOCUMENTS

DD    282616 A5    9/1990

(Continued)

*Primary Examiner*—Kevin C Sirmons
*Assistant Examiner*—Bhisma Mehta
(74) *Attorney, Agent, or Firm*—Bose McKinney & Evans LLP

(57) ABSTRACT

The invention concerns an array and a method for dosing a hormone regulating the blood glucose, especially insulin, of a diabetic patient. In order to improve the administration of the hormone, the invention provides the following characteristic combination: a first sensor for measuring tissue glucose level; a controller having as an input the measured tissue glucose level from the first sensor, the controller having a control algorithm to determine an amount of hormone to be dosed based upon the measured tissue glucose level; a hormone dosing unit connected to the controller and automatically administering a hormone dose based upon a signal received from the controller; a second sensor for measuring an influencing patient variable; a pilot control device connected to the second sensor, the pilot control device connected to and forming a circuit with the controller, the pilot control device acting on the controller in accordance with the influencing patient variable that is measured by the second sensor, whereby the pilot control device reduces dead time of the controller.

21 Claims, 1 Drawing Sheet

U.S. PATENT DOCUMENTS

| | | | |
|---|---|---|---|
| 4,475,901 A | | 10/1984 | Kraegen et al. |
| 4,731,726 A | | 3/1988 | Allen, III |
| 5,190,041 A | | 3/1993 | Palti |
| 5,497,772 A | * | 3/1996 | Schulman et al. ............ 600/347 |
| 5,558,640 A | | 9/1996 | Pfeiler et al. |
| 5,665,065 A | * | 9/1997 | Colman et al. ................ 604/66 |
| 7,556,613 B2 | * | 7/2009 | Wittmann et al. ............. 604/65 |

FOREIGN PATENT DOCUMENTS

| | | |
|---|---|---|
| DE | 19756872 | 7/1999 |
| EP | 1039941 B1 | 7/2003 |

* cited by examiner

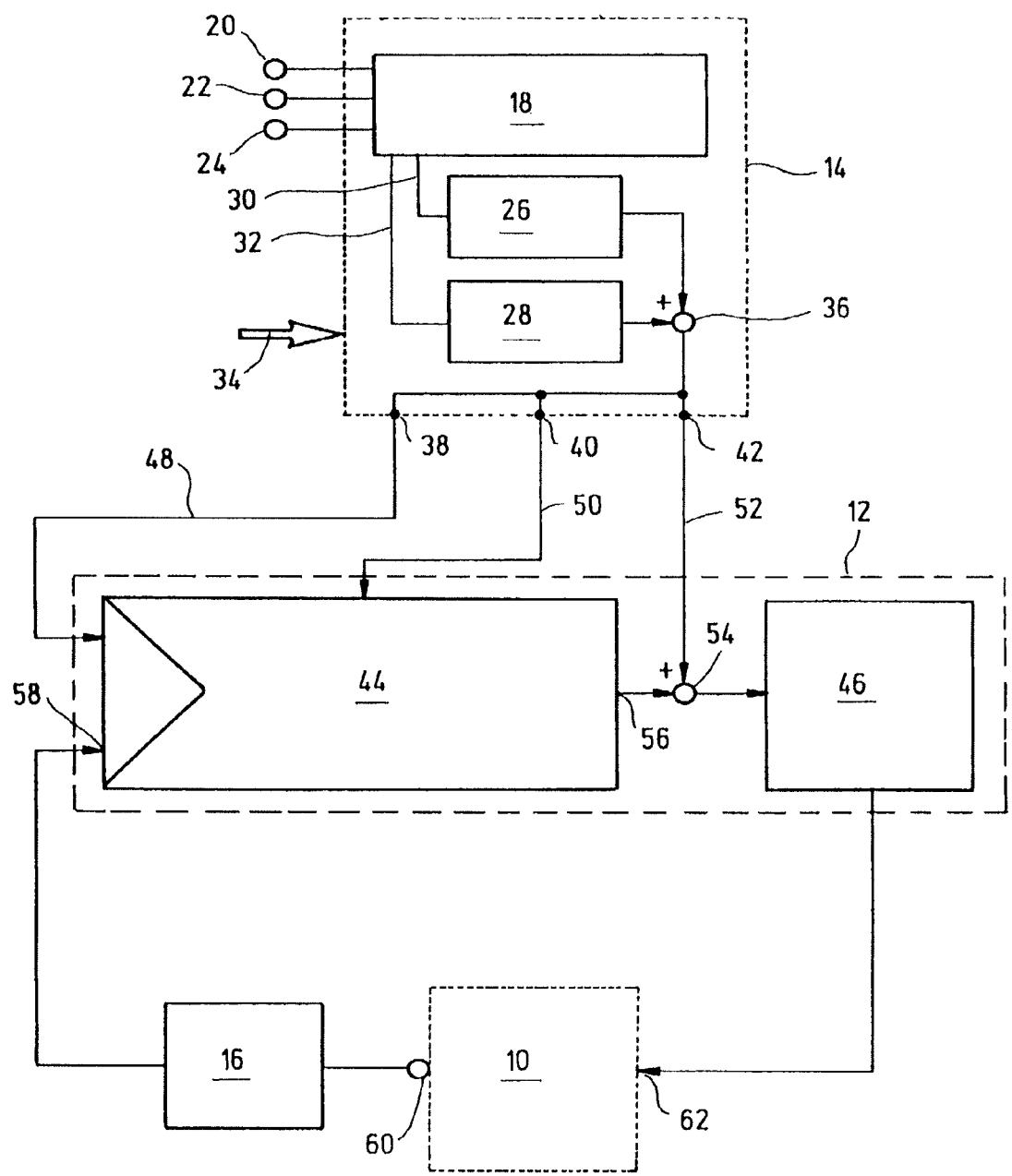

ARRAY AND METHOD FOR DOSING A HORMONE REGULATING BLOOD SUGAR IN A PATIENT

RELATED APPLICATION

This application is a continuation application of U.S. patent application Ser. No. 10/203,673, filed Nov. 18, 2002, now U.S. Pat. No. 7,556,613, which is a national stage application of International Application PCT/EP01/00625, filed Jan. 20, 2001, which claims priority to DE 10006044.7, filed Feb. 10, 2000, all of which are incorporated by reference herein.

DESCRIPTION

The invention concerns an array and a method for dosing a hormone, in particular insulin, which is suitable for regulating blood glucose in a patient.

Diabetes mellitus is a metabolic disease in which the regulation of the glucose content of blood to a level appropriate for intermediary metabolic requirements is disturbed by a deficiency in insulin. Conventionally diabetes patients counteract an increase in the glucose concentration by injecting exogenous insulin. The amount to be administered is determined empirically on the basis of blood sugar self tests. It has already been proposed to improve the sugar determination by taking samples in fat tissue continuously or at intervals by means of a microdialysis probe and automatically evaluating the tissue glucose level as a measure for blood glucose.

DD 282 616 A5 describes a device for the load-adjusted control of infusion pumps whose insulin supply to the diabetic is either controlled automatically by a blood glucose sensor or semi-automatically by means of a microcomputer using patient-specific insulin dosage profiles. The input side of the microcomputer is coupled to a heart rate sensor in order to switch between so-called positive and negative insulin glucose characteristics when a threshold is exceeded. Hence during a load situation this enables a time-dependent reduction of the dosage according to an empirical function i.e. a lowering of the plasma insulin concentration, instead of the sensory control.

It is known from EP-A 0 824 240 that so-called individual-specific insulin activity equivalents can be determined with the aid of a computer from exercise heart rate data based on a physiological model of glucose/insulin metabolism which are intended to be used for learning and training programs as well as in further education.

With this as the starting point the object of the invention is to provide an array and method of the type stated above which improves the dosage of a hormone influencing blood glucose and can be optimized by taking into account the patient's condition. In particular it should enable the patient to keep his blood sugar level permanently in the normoglycaemic range by appropriate hormone doses.

The combination of features stated in the claims is proposed to achieve this object. Advantageous embodiments and further developments of the invention follow from the dependant claims.

The essence of the invention is to provide a controlling means for the fine regulation of the hormone dosage in which influences that can only be detected by the control with a time shift are at least partially compensated by anticipating coarse pre-control. Correspondingly a system having the following features is proposed according to the invention:
- a measuring device for detecting measured values correlatable with blood glucose;
- a controlling means which comprises a controller to process the measured values according to a control algorithm and a hormone dosing unit to administer a hormone dose; and
- a pilot control device (14) acting on the controlling means (12) to reduce the dead time of the control.

The coarse pre-control can considerably improve the control performance. In particular changes in the metabolic state caused by external influences or transport processes inside the body can be taken into account in a quasi anticipating manner without a dead time so that deviations remain limited to a small range and excessive glucose values are avoided a priori. This allows an optimal dosage to be obtained for adjusting a normoglycaemic blood glucose level.

This can be advantageously achieved by the pilot control device having an anticipatory action on the controlling means in accordance with an influencing variable that is detected by sensors.

According to a particularly preferred embodiment of the invention the degree of physical activity of the diabetic is taken into consideration by the pilot control device having an activity measuring unit for the sensory detection of the degree of physical activity of the patient. With regard to the differentiated detection of resting states of the patient such as lying, sitting, standing, an advantageous embodiment provides that the pilot control device has a position sensor and in particular a mercury switch or spirit level. In order to detect states of movement it is advantageous when the pilot control device has a movement sensor in particular a pedometer. Also with regard to an indirect detection of physical strain it is advantageous when the pilot control device has a sensor for detecting body parameters of the patient such as heart rate, body temperature or skin conductivity.

A further preferred embodiment of the invention provides that the pilot control device has a basal control element for the continuous pre-administration of a preferably patient-specific basal dose of the hormone. This would cover an existing basic requirement while the controller remains at a favorable working point. A further improvement is achieved by the basal control element having a correction stage to adapt the basal dose to changes in the hormone sensitivity of the patient during the day. In order to also correct for the exogenous glucose surge it is of particular advantage when the pilot control device has a bolus control member to pre-administer hormone boli depending on the food intake of the patient. It is also advantageous for the pilot control device to have a timer for the time-dependent determination of the basal dose or to determine the time for administering the hormone boli. In order to be able to additionally take into consideration the influence of physical activity in the basal and bolus dose it is advantageous when the basal control element and/or bolus control element are connected downstream of the activity measuring device. A further advantageous embodiment provides that the pilot control device has an input unit to enter data and in particular the times of day and bread units of the patient's food intake.

The pilot control device can act on the controlling means by having a set-point output connected to the controller in order to pre-set a command variable. Other advantageous methods are to connect the pilot control device and the controller on the output side via a summation element to the hormone dosage unit or to provide the pilot control device with means for selecting the control algorithm or to pre-set control parameters of the controller.

In order to prevent operating errors it is proposed that the pilot control device has a monitoring stage that monitors and limits the hormone dose, optionally after registering critical conditions of the patient such as abnormal body temperature.

According to a further advantageous embodiment of the invention the measuring device has a glucose sensor which preferably utilizes microdialysis technology to detect tissue glucose values as measured values. This allows a continuous detection of the regulating variable without having to maintain a direct access to the blood circulation. In this case the pre-control is particularly advantageous since the glucose transfer between blood and tissue occurs with a certain delay.

Provided the hormone to be administered is insulin, the operating range of the controller should be limited to positive values. It would also be fundamentally possible to utilize a negative operating range by dosing counter-insulin hormones such as glucagon. In any case it is advantageous when the pilot control device acts on the controlling means while maintaining an adjustment reserve.

In view of the special characteristics of glucose metabolism an optimal control behavior or control result can be achieved by designing the controller as a condition controller in which the control algorithm has a program routine acting as observer of the measured values and hormone dosage values in order to estimate non-measurable variables of state and in which the controller has a proportional-integral element to deal with disturbance variables.

It is proposed that the hormone dosage unit comprises a dosage pump designed for preferably subcutaneous hormone infusion as the actuator of the controlling means. For safety reasons the control loop can be closed by a deliberate act of the patient preferably in that the hormone dosage unit has a triggering element to manually confirm a planned hormone administration. It is also basically conceivable with regard to reducing the risks that the hormone dosage unit is only designed to display and/or provide or measure a hormone dose which is administered by the patient himself.

In order to allow the patient to have a flexible lifestyle an advantageous embodiment provides that the measuring device, the controlling means and the pilot control device are in the form of a small portable instrument that can be carried on the body of the patient.

The aforementioned object is achieved with regard to the process in that:
  measured values that can be correlated with blood glucose are detected;
  the measured values are fed to a controlling means in which a controller processes the measured values according to a control algorithm and outputs a hormone dose to a hormone dosage unit; and
  the controlling means (12) for the fine dosing of the hormone is pre-controlled by a pilot control device (14) to reduce the dead time.

The invention is further illustrated in the following on the basis of the operating example shown schematically in the drawing. The single FIGURE shows a block diagram of an array and a system for controlled insulin dosing.

The array shown in the FIGURE enables an automatic regulation of the blood glucose of a diabetes patient 10. It is essentially composed of a controlling means 12 for the fine adjustment of the insulin administration, a pilot control device 14 for the coarse pre-control of the controlling means 12 in accordance with at least one influencing or disturbing variable which influences the blood glucose level of the patient 10 and a measuring device 16 for the sequential detection of measured values that correlate with the blood glucose level.

The pilot control device 14 has an activity measuring unit 18 for the sensory detection of the degree of physical activity of the patient as an influencing variable. For this purpose the input side of the activity measuring unit 18 is connected to a suitable position sensor 20 to detect resting states of the patient. The positioning sensor 20 can for example be in the form of a mercury switch or crossed spirit levels to enable detection of the inclination i.e. whether the patient 10 is lying, sitting or standing. Furthermore a movement sensor 22 is additionally provided which sends suitable signals to the activity measuring unit 18 to detect movement states of the patient 10. A pedometer can be used for this in order to quantify the physical activity when walking or running. A further sensor 24 is used to detect body parameters of the patient which at least indirectly allow conclusions about physical activity i.e. in particular heart beat frequency, body or skin temperature and skin conductivity.

The pilot control device 14 additionally comprises a basal control element 26 to determine a basal rate or basal dose which is suitable for covering the basal insulin requirement of the patient. For this purpose the basal control element 26 can have a correction stage (which is not shown) to adjust the basal dose to a peripheral insulin sensitivity which changes with time. For example the basal dose can be changed depending on the time of day according to a ramp function. In order to compensate for a food-related exogenous glucose surge as an influencing variable the pilot control device 14 has a bolus control element 28 which pre-sets insulin boli or insulin dosages that are adapted to the food intake. For this purpose a timer or clock (which are not shown) can be provided to determine the time to administer the insulin dose or for the diurnal time control of the basal rate. The control elements 26, 28 are superimposed via signal paths 30, 32 onto the activity measuring unit 18 to allow an activity-related weighting of the basal and boli doses. An input unit 34 of the pilot control device 14 enables input of additional data such as times of day and bread units of the patient's food intake to be processed in addition to the signals registered by the sensors. On the output side the control signals or output data of the control elements 26, 28 that are brought together by the summation element 36 are optionally fed to one of the outlets 38, 40, 42 of the pilot control device 14.

There are various ways in which the pilot control device 14 can have a corrective action on the controlling means 12 comprising a controller 44 and a dosage device 46. A command variable that cannot be influenced by the control system and which determines the (time-dependent) set-point time course can be fed via the signal path 48 to the controller 44. The data path 50 allows selection of a suitable control algorithm or variation of the control parameters. To achieve a direct action on the dosage unit 46 the controlling output 42 of the pilot control device 14 can be additively superimposed on the controller output 56 via the line 52 and the summation element 54. The said measures allow a limitation of the control range while the controlling means undertakes the fine dosing. In addition it is also expedient to monitor the insulin dose to be administered and to check that plausibility criteria are adhered to. This is achieved by a monitoring stage that is not shown which optionally also registers critical patient conditions such as disease for example on the basis of body temperature. In this connection the maintenance of a reserve for adjustment and control should also be ensured by appropriate limitation of the output variables of the pilot control device 14.

The pilot control device 14 influences the controlling means 12 in an open action sequence i.e. the controlled output variable (finally the insulin dose) does not have a return effect on the controlling influencing variable (for example the degree of activity of the patient). The influencing control is achieved in an anticipating or pre-controlling manner in the sense of an immediate correction of the disturbing influence without first waiting for a change in the control variable. In contrast the control system operates basically in a closed circuit in which the variable to be adjusted has a retroaction on the measured quantity.

With regard to hardware the pilot control device 14 and the controller 12 are in the form of an application-specific integrated semi-conductor circuit or a suitable processor system and in particular a microcontroller connected to a digital signal processor. On this there is a state controller which has a high control performance in which, in contrast to conventional output variable control, there is a feedback of the state variables of the control path. In order to estimate state variables which cannot be directly measured, the control algorithm has a program routine acting as observer of the measured values and the stated dosage. In addition a proportional-integral element is used to deal with interfering effects such as exogenous glucose surges. In order to synthesize such a control algorithm the blood glucose metabolism is described as a mathematical model by a linear differential first order equation system in which transport and lag time effects are taken into account by proportional delaying (PTI) terms. However, it would have also been fundamentally possible to use a simple PID controller instead of the previously described state controller.

The input 58 of the controller 44 is connected to the measuring device 16 to feed in the actual or measured values of the control variable. The blood glucose level is not measured directly due to the difficulties of a permanent intravenous access, but rather the correlatable tissue glucose level in the subcutaneous fatty tissue of the patient 10. For this purpose the measuring device 16 has a glucose sensor 60 which utilizes microdialysis technology in a known manner. For this a microdialysis probe implanted in the tissue is supplied with a perfusion liquid and the glucose content is detected sequentially by an electrochemical-enzymatic electrosensor connected downstream. The measured values can be derived quasi-continuously or at intervals.

The dosage unit 46 provided as an actuator comprises an insulin pump which enables an automatic subcutaneous insulin application via an infusion cannula 62 for example in the stomach region. The microdialysis probe as well as the infusion cannula can be implanted by the patient himself without medical supervision. The time delays occurring in the control due to transfer from blood to subcutaneous tissue can be managed without problems by the proposed control strategy. The entire control array can be accommodated in a portable instrument carried on the body of the patient which thus undertakes the function of the pancreas for normoglycaemic metabolic control.

The invention claimed is:

1. An array for dosing a hormone suitable for regulating blood glucose of a patient, comprising:
    a first sensor for measuring tissue glucose level;
    a controller having as an input the measured tissue glucose level from the first sensor, the controller having a control algorithm to determine an amount of hormone to be dosed based upon the measured tissue glucose level;
    a hormone dosing unit connected to the controller and automatically administering a hormone dose based upon a signal received from the controller;
    a second sensor for measuring an influencing patient variable;
    a pilot control device connected to the second sensor, the pilot control device connected to and forming a circuit with the controller, the pilot control device having a corrective action on the controller based on the influencing patient variable that is measured by the second sensor, whereby the pilot control device reduces dead time of the controller in responding to changes in the patient's blood glucose level.

2. The array of claim 1, wherein an operating range of the controller is limited to positive values when the hormone is insulin.

3. The array of claim 1, wherein the pilot control device acts on the controller while maintaining a reserve for adjustment of the hormone dose to be administered.

4. The array of claim 1, wherein the controller is a state controller having a control algorithm.

5. The array of claim 1, wherein the controller has a proportional-integral element to address disturbance values.

6. The array of claim 1, wherein the hormone dosing unit comprises a dosage pump designed for subcutaneous hormone infusion.

7. The array of claim 1, wherein the first sensor, the controller and the pilot control device comprises a small portable instrument that can be carried on the patient's body.

8. The array of claim 1, wherein the pilot control device comprises mercury switches.

9. The array of claim 1, wherein the pilot control device has spirit levels.

10. The array of claim 1, wherein the second sensor comprises a position sensor to detect resting states of the patient.

11. The array of claim 1, wherein the second sensor detects body parameters of the patient.

12. The array of claim 1, wherein the second sensor comprises a movement sensor.

13. The array of claim 1, wherein the second sensor comprises a skin conductivity sensor.

14. The array of claim 1, wherein the second sensor comprises at least two individual sensors, each of which measures a different influencing variable selected from position, movement, heart rate, body temperature and skin conductivity of the patient.

15. The array of claim 1, wherein the second sensor comprises an activity measuring unit for the sensory detection of a degree of physical activity of the patient.

16. The array of claim 1, wherein the pilot control device comprises a basal control element for continuous pre-administration of a basal dose of the hormone.

17. The array of claim 1, wherein the pilot control device has a timer.

18. The array of claim 1, wherein the pilot control device has a set-point output connected to the controller in order to pre-set a command variable.

19. The array of claim 1, wherein the pilot control device and the controller are connected on an output side via a summation element to the hormone dosing unit.

20. The array of claim 1, wherein the pilot control device is configured to select the control algorithm or to pre-set parameters of the controller.

21. The array of claim 1, wherein the pilot control device comprises a monitoring stage to monitor and limit the hormone dose.

* * * * *